United States Patent [19]

Cowfer et al.

[11] Patent Number: 4,642,400
[45] Date of Patent: Feb. 10, 1987

[54] PROCESS FOR FINISHING VINYL CHLORIDE MONOMER

[75] Inventors: Joseph A. Cowfer, Medina, Ohio; James E. Best, Paducah, Ky.

[73] Assignee: The B. F. Goodrich Company, Akron, Ohio

[21] Appl. No.: 779,337

[22] Filed: Sep. 23, 1985

[51] Int. Cl.[4] ............................................. C07C 17/38
[52] U.S. Cl. ..................................... 570/238; 570/226
[58] Field of Search ................... 570/238, 226; 526/77

[56] References Cited

U.S. PATENT DOCUMENTS 3,830,859  8/1974  Gordon et al. ...................... 570/238
3,846,253  11/1974  Obrecht ............................... 570/238

FOREIGN PATENT DOCUMENTS 794410  5/1958  United Kingdom ................. 570/238

Primary Examiner—Natalie Trousof
Assistant Examiner—Joseph A. Boska
Attorney, Agent, or Firm—A. D. Lobo; A. A. Csontos

[57] ABSTRACT

This process stems from the discovery that the solubility of water in vinyl chloride monomer ("VCM") is so low in a cold aqueous caustic solution at a temperature below 0° C., that the aqueous solution will remove water dissolved in the monomer, and at the same time, will neutralize the HCl associated with the monomer and prevent the formation of acetylene. This discovery makes it possible to dry and neutralize a HCl and water-containing vinyl chloride ("VCl") stream, by intimately contacting the stream with a cold aqueous 2 to 30 wt % caustic soda solution at a temperature below 25° F. and above the freezing point of the caustic solution. In a commercial VCM producing facility, VCl can be "finished" in a "stand-alone" processing facility with greater economy than in a conventional VCM plant, yet avoid the hazards of operating a conventional VCl stripping column and scrubbers packed with solid caustic pellets. The process allows simultaneously drying and neutralizing a VCl stream containing from about 1 part per million (ppm) to about 500 ppm HCl, and from about 10 ppm to about 300 ppm of water by contacting it with a 10% to 25% aqueous cold caustic solution, and separating dry and neutralized VCM monomer containing no more than 100 ppm water.

6 Claims, 3 Drawing Figures

PROCESS FOR FINISHING VINYL CHLORIDE MONOMER

BACKGROUND OF THE INVENTION

Few monomers are commercially produced in the world on so large a scale as vinyl chloride monomer ("VCM"). The U.S. production alone of VCM was about 7.7 billion pounds in the year 1984, most of which was used in the production of poly(vinyl chloride), the remainder was used for the production of copolymers of VCM with vinylidene chloride, graft copolymers of vinyl chloride on methylmethacrylate, polybutadiene, ethylene-propylene elastomer, etc.

Despite this scale of production, not much attention has been accorded the exacting requirements for the commodity VCM, except of course by those charged with the responsibility of producing on-spec product VCM. Product VCM, referred to as "finished" VCM, is limited to the following: HCl 0.5 parts per million (ppm) by weight; acetylene ($C_2H_2$) 0.2 ppm; caustic (NaOH) 0.3 ppm; and, water 100 ppm. Many drugs for human consumption have less stringent purity specifications.

As of the present time, VCM produced in a conventional commercial VCM plant is derived from vinyl chloride VCl in the overhead of a VCl distillation column which overhead typically contains from about 50–500 ppm HCl and 10–300 ppm water. This VCl overhead, after it is condensed, is stripped in a stripping column to reduce the level of HCl which is taken overhead. The bottoms from the stripper, still containing in the range from about 1–50 ppm HCl, is scrubbed either by contact with caustic solution, or by upflow percolation through a bed of solid caustic.

The term "vinyl chloride monomer" (VCM) is used when the VCl has been purified, that is "finished", so that it meets product VCM specifications.

Those operating a VCM plant utilizing such a process, recognize that corrosion is the overriding problem in the stripping column. This problem is exacerbated because the corrosion process contributes ferric salts to the VCM. This is an impurity, among others, which can victimize an otherwise meticulously operated polymerization process because it produces off-spec poly(vinyl chloride).

The maintenance of solid caustic scrubbing beds is an unenviable task due to VCl emissions when the beds are opened to be recharged with fresh caustic pellets. Moreover, because of their very nature, they are subject to channeling and variability in contact efficiency even when channeling is minimal. The result is that the purity of the VCM is unreliable. To overcome the problem, the beds are greatly overdesigned. A concomitant of overdesigning the beds is the added risk of generating acetylene due to dehydrochlorination of VCl in "hot spots" in a caustic bed.

This problem of acetylene formation was recognized and addressed in a purification process for VCM disclosed in Japanese Pat. No. 57/2009234 A2 (12/22/82) which process removed HCl without forming acetylene byproduct by passing the liquid VCl through a column packed with a porous powder of an alkaline earth metal hydroxide or oxide, optionally supported on silica or alumina, with an avg. particle diam. of 3.5 mm and surface area 4.5 $m^2/g$.

Some commercial plants utilize caustic wash scrubbers in which the VCl from either the overhead of the vinyl chloride column, or the bottoms of the vinyl chloride stripper, is scrubbed by contact with an aqueous solution of NaOH at ambient temperature. But there was no reason for these plants to operate at sub-25° F. temperatures, since it was known that the solubility of water in VCM at temperatures as low as $-12°$ C. (10° F.) was 230 ppm (see "Solubility of Water in Vinyl Chloride" by Clarke, C. E. et al Can. J. Chem., 59(5), 768–71 1981). As will readily be appreciated, there was no logical reason to expect that a solubility of 230 ppm of water in VCM at 10° F. would lead to the use of a cold caustic solution to dry VCl so that it contains less than 100 ppm water, and meet the 'water spec' for VCM.

As will presently be apparent from the data presented hereinafter, it was discovered that the solubility of water in VCM drops off when there is caustic solution present, and the caustic solution is at a temperature below about 25° F.($-3.89°$ C.). It is this unexpected phenomenon which is the basis for the process of this invention.

As one would expect, the low temperature does not adversely affect the ability of the NaOH to neutralize the HCl present, but it unexpectedly suppresses the formation of by-product acetylene. Coincidentally, though the difference in specific gravities of the VCM and caustic solution diminishes with decreasing temperature, it is sufficiently large at a temperature below $-4°$ C. to permit a separation of the VCM and aqueous phases which separation is effected in a settling tank.

It was never realized that the low solubility of water in cold VCM was the key to using an aqueous stream to dry VCl. Washing wet VCl with cold caustic made it possible to meet the stringent specifications of product VCM. It is this singular effect of temperature on the solubility of water in VCM which permits the effective and reproducibly reliable results obtained with the process of this invention.

Further, the solubility of Na in VCM and that of water in VCM are such that it is possible to meet the stringent specifications of product VCM. It is these physical parameters of the components which permit the effective and reproducibly reliable results obtained with the process of this invention.

SUMMARY OF THE INVENTION

It has been discovered that the solubility of water in vinyl chloride monomer ("VCM") is so low in a cold aqueous caustic solution at a temperature below 0° C., that the aqueous solution will remove water dissolved in the monomer, and at the same time, will neutralize the HCl associated with the monomer and prevent the formation of acetylene.

It is therefore a general object of this invention to dry and neutralize a HCl and water-containing vinyl chloride ("VCl") stream, by intimately contacting the stream with a cold aqueous 2 to 30 wt % caustic soda solution at a temperature below 25° F. and above the freezing point of the caustic solution.

It has also been discovered that a VCl stream in a commercial vinyl chloride producing facility can be "treated" in a "stand-alone" processing facility with greater economy than in a conventional VCM plant, yet avoid the hazards of operating a conventional VCl stripping column and scrubbers packed with solid caustic pellets.

It is a specific object of this invention to provide a process for simultaneously drying and neutralizing a VCl stream containing from about 1 part per million (ppm) to about 500 ppm HCl, and from about 10 ppm to about 300 ppm of water by contacting it with a 10% to 25% aqueous cold caustic solution, and separating dry and neutralized VCM monomer containing no more than 100 ppm water.

BRIEF DESCRIPTION OF THE DRAWINGS

The foregoing and other objects and advantages of our invention will appear more fully from the following description, made in connection with the accompanying drawings of preferred embodiments of the invention, wherein like characters refer to the same or similar equipment.

DETAILED DESCRIPTION OF A PREFERRED EMBODIMENT

In the preferred embodiment, this invention relates to the vinyl chloride ("VCl") purification portion of a commercial plant. Purification of VCl, to produce product VCM, is a principal step in the operation of a balanced VCl process (see *Encyclopedia of Chemical Technology* by Kirk & Othmer, Chap. titled "Vinyl Polymers (Vinyl Chloride)" Vol 23, pg 870, 3d ed. John Wiley & Sons) details of which are well known and incorporated by reference thereto as if fully set forth herein. However, very little is stated about the difficulty of meeting the specifications for product VCM and how this is conventionally accomplished.

For the purpose of clarity, the term "vinyl chloride" (VCl) is used herein when the vinyl chloride is in-process, that is, first formed and subsequently processed in the VCl purification section. The term "vinyl chloride monomer" (VCM) is used when the VCl has been purified, that is finished, so that it meets product VCM specifications.

Figure 1:
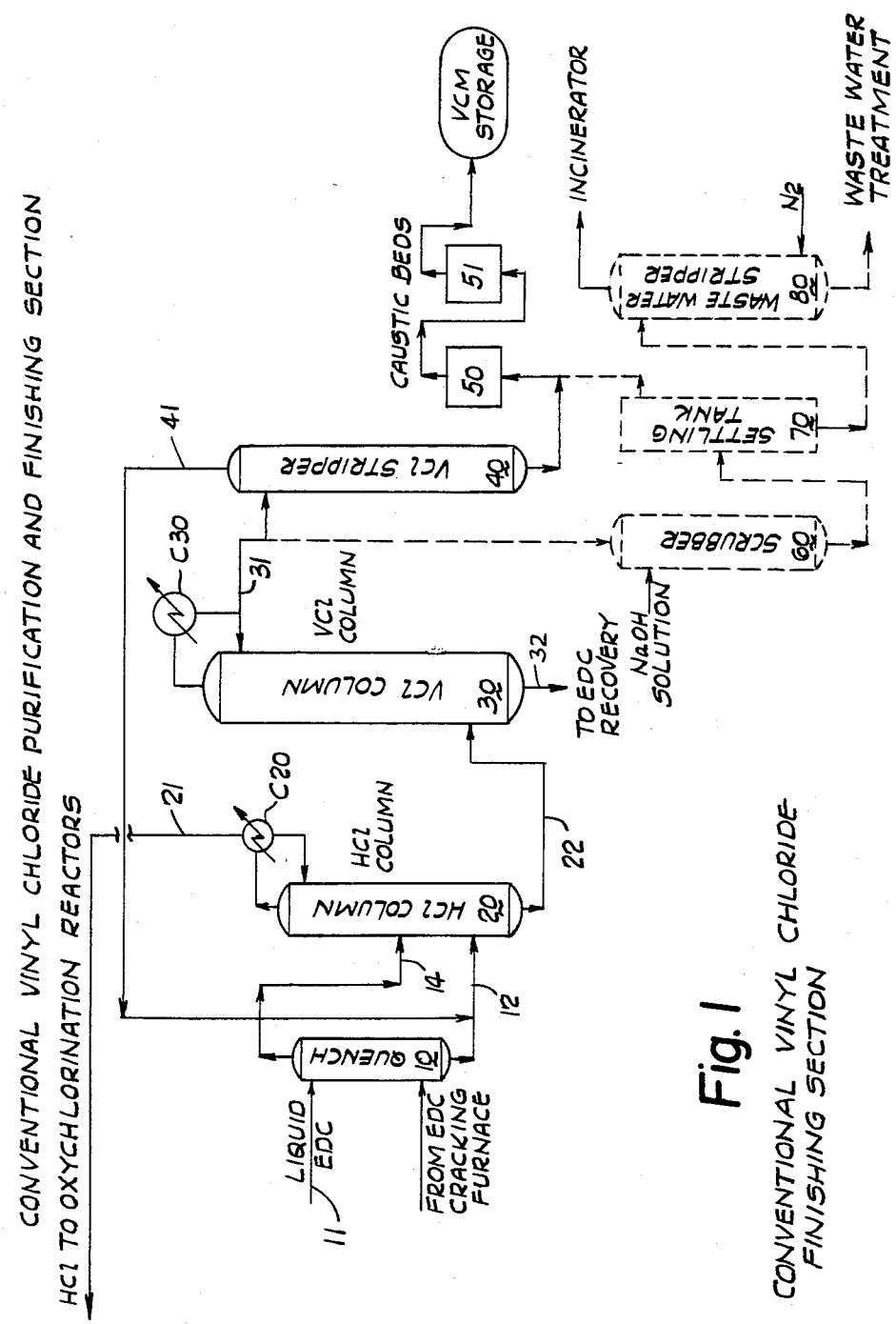
FIG. 1 is a process flowsheet of a conventional purification section in a commercial plant for the production of vinyl chloride monomer from ethylene dichloride.

Referring to FIG. 1 there is shown a simplified flowsheet schematically illustrating a conventional purification system in which the effluent from an ethylene dichloride ("EDC") cracking furnace (not shown) is quenched in a quench tower 10 with liquid EDC introduced near the top through line 11. The liquid from the bottom of the quench tower is led through line 12 into the bottom of a HCl distillation column 20; and overhead from the quench tower is led through line 14 into the upper portion of the column to remove HCl. The HCl comes off overhead and is condensed in condenser C20; a portion is refluxed to column 20 and the remainder recycled through line 21 to reactors used in the oxychlorination portion of the VCl plant. The bottoms from column 20 is a moisture-containing VCl-rich stream which is flowed through line 22 to a VCl column 30.

The overhead from the VCl column 30 is moisture-containing VCl which is condensed in condenser C30 and a portion refluxed to column 30, the remaining portion being flowed through line 31 to a VCl stripper 40. All liquid lines are under pressure since the boiling point of VCl under atmospheric presure is 8° F. A line 32 carries the bottoms from the column 30 to a EDC recovery section where unconverted EDC is recovered for recycle to the cracking furnace. This is done, typically, by conventional distillation; the result is the separation of the lights and heavy ends.

The impure VCl from the overhead of the VCl column is conventionallly purified in one of two ways. In one (first) method, the impure VCl is first stripped, then dried; in the other (second) method, the impure VCl is directly scrubbed with an aqueous caustic solution and then dried.

Referring to the first method utilizing equipment which is illustrated in FIG. 1 in solid outline, the VCl stripper 40 is operated to strip additional HCl in the stream, along with some VCl, which are removed overhead and recylced to the HCl column 20 through line 41. The HCl removed includes HCl carried over with the bottoms from the HCl column 20, and also HCl generated in the reboiler of the VCl column 30 because of breakdown of EDC. The bottoms from the stripper 40 is wet VCl which is flowed upward through solid caustic dryers 50 and 51 which are beds of solid caustic pellets, sequentially, to remove enough HCl to meet the specification, and then to dry the wet VCl for product VCM. The advantage of using a VCl stripper is that the HCl taken overhead can be recycled to the HCl column and recovered.

In those instances where no VCl stripper is used, referring to the second method illustrated in the alternate schematic shown in phantom outline, the impure VCl from the overhead of VCl column 30 is directly scrubbed with aqueous caustic solution at ambient temperature in scrubber 60. The bottoms from the scrubber 60 is allowed to settle in settling tank 70 and the supernatant VCl is removed overhead and dried through the solid caustic dryers 50 and 51, as described hereinabove. The advantage of avoiding the use of a VCl stripper and directly scrubbing with aqueous caustic, is to use smaller caustic dryers which require less frequent recharging with fresh solid caustic; that is, to minimize the cost of solid caustic which is much more expensive than caustic solution. In the drawing, the same caustic dryers are shown for each of the methods, for convenience.

Bottoms from settling tank 70 are stripped in a waste water stripper 80 with an inert gas, preferably nitrogen introduced in the bottom. The bottoms from the stripper 80 are led to a waste water treatment facility and disposed of in a suitable manner.

Figure 2:
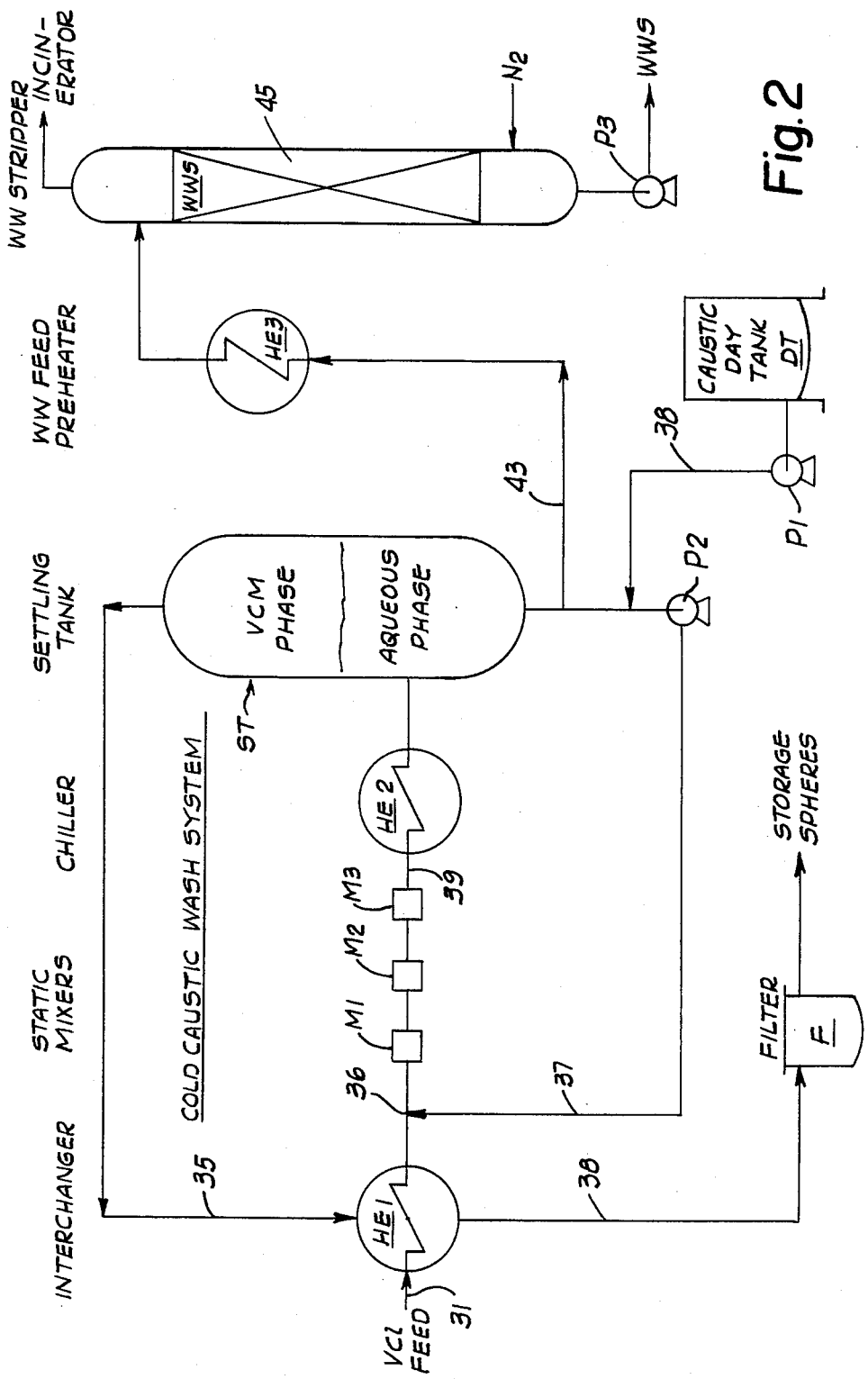
FIG. 2 is a flowsheet of the novel process of this invention utilizing a purification section without conventional dryers.

Referring now to FIG. 2 there is schematically illustrated a simplified flowsheet of a modified VCM plant in which a cold caustic wash is used to purify a VCl stream 31 which is the overhead from VCl column 30 (as shown in FIG. 1), it being understood that the process flow in the plant, up to this point, and the process flow for providing the VCl bottoms, is the same as described in FIG. 1. In the novel modified system, no VCl stripper is used, and no solid caustic (pellet) beds are used to dry the wet VCl because the wet VCl is dried by contact with cold concentrated aqueous NaOH.

Though the concentration of the caustic solution is not narrowly critical, the higher the concentration, the more effective is the phase separation between the aqueous and organic phases. Further, the higher the concentration, the larger the amount of HCl breakthrough that can be neutralized when such a breakthrough does accidentally occur. Not the least important is that the solubility of VCM in the caustic decreases with increasing NaOH concentration.

The VCl liquid stream 31, typically at a temperature in the range from about 80°–120° F., is cooled to a temperature in the range from about 15°–40° F. in shell-and-tube heat exchanger HE1 by countercurrent heat exchange with cold, "finished" VCM monomer introduced through line 35 in the shell side of HE1. The object, of course, is to use the VCM stream 35 to chill the incoming VCl feed as much as can economically be accomplished before it is further chilled by mixing, in a mixing tee 36, with cold conc. caustic solution introduced through line 37.

The amount of NaOH solution to be mixed with the VCl feed is sufficient to neutralize the HCl in the feed so that there is less than 0.5 ppm HCl left in the product VCM recovered; the amount is also sufficient to extract the water dissolved in the organic phase into the aqueous phase. Typically, the amount of NaOH solution contains more than 100 times as much NaOH than there is HCl in the VCl, on a weight basis. It will be evident that the major portion of the NaOH solution to the mixing tee 36 is provided by recycle from the settling tank, and the make-up from the caustic day tank DT supplies the remainder which is proportional to the conc of HCl in the VCl to be finished. The finished VCM which has been heated in HE1 is led through a filter F to storage spheres.

The conc. caustic solution is preferably in the range from about 2 to 35% NaOH, and more preferably from about 15–25%, for reasons relating to the solubility parameters presented hereinafter, of the solutions. Though NaOH is most preferred for economic reasons it will be appreciated any alkali metal hydroxide may be used, though the solubility parameters of KOH and LiOH will not be the same as those of NaOH, and the optimum concentrations and temperatures at which each is used will be determined by a little trial and error such as one skilled in the art would routinely undertake.

The make-up caustic is introduced to line 37 from a caustic day tank DT, through line 38, by pumps P1 and P2. As will readily be apparent, all the equipment used in the process illustrated in FIG. 2 is insulated to maintain the economy of the process.

Since the function of the cold caustic solution is both to neutralize the HCl in the VCl stream 31, and also to remove the moisture from the VCl, it is essential that the streams 31 and 37 be intimately mixed. This is effected by one or more static mixers, preferably three static mixers M1, M2 and M3 in series, from which line 39 introduces the VCl/caustic mixture into the tube side of a refrigerated shell-and-tube heat exchanger HE2. The effect of the mixers is to provide an intimate mixture of the vinyl chloride organic phase and the aqueous caustic phase. The VCl is broken up into droplets having a diameter in the range from about 10 microns to about 1000 microns, and more preferably from 50–100 microns.

The VCl/caustic mixture emerges from HE2 at a temperature in the range from about 0°–25° F., more preferably 5°–15° F. Those skilled in the art will presently realize that, given the solubility of water in VCM as a function of temperature (presented hereinbelow), only as much refrigeration in the shell side of HE2 is provided as is necessary to dry the VCM to the moisture specification demanded.

The cold, preferably about 10° F. VCl/caustic mixture is flowed into a large settling tank ST where a phase separation takes place. The residence time is not narrowly critical but should be sufficient to allow the distinct formation of separate organic and aqueous phases. Typically a residence time in the range from about 1 min to about 30 min is desirable, and more preferably from about 5 min to about 20 min.

The supernatant phase is dried product VCM, and the lower phase is caustic solution diluted with aqueous NaCl. Though effecting and utilizing such a phase separation is not an economically attractive unit operation because the specific gravities (sp gr) of dilute caustic and VCM are very close at ambient temperature, the separation is unexpectedly effective with conc. aqueous cold caustic and cold NaCl solutions.

The sp gr of VCM, and aqueous NaOH and NaCl solutions as a function of temperature, are presented in the tables hereinbelow. Details of how the measurements were made are set forth hereinbelow.

TABLE I

| wt % NaOH | sp gr @ 0° C. | sp gr @ 15° C. |
|---|---|---|
| 1 | 1.0124 | 1.0106 |
| 2 | 1.0244 | 1.0220 |
| 4 | 1.0482 | 1.0444 |
| 8 | 1.0943 | 1.0889 |
| 12 | 1.1399 | 1.1333 |
| 16 | 1.1849 | 1.1776 |
| 20 | 1.2296 | 1.2218 |
| 24 | 1.2741 | 1.2658 |

TABLE II

| wt % NaCl | sp gr @ 0° C. | sp gr @ 15° C. |
|---|---|---|
| 1 | 1.0075 | 1.0071 |
| 2 | 1.0151 | 1.0144 |
| 4 | 1.0304 | 1.0292 |
| 8 | 1.0612 | 1.0591 |
| 12 | 1.0924 | 1.0895 |

TABLE III

| Sp Gr of VCl as a function of Temperature | |
|---|---|
| Temp. °F. | sp gr |
| 0 | 0.98 |
| 10 | 0.97 |
| 20 | 0.96 |
| 30 | 0.95 |
| 40 | 0.94 |
| 50 | 0.93 |

The lower aqueous phase from the settling tank ST is a waste water stream which is flowed through line 43 to shell-and-tube heat exchanger HE3, through the tube sides thereof, in countercurrent heat exchange flow with a hot fluid, preferably low pressure steam to heat the waste water to a temperature in the range from about 160°–200° F. before it is introduced into a waste water stripper WWS, near the top thereof so as to trickle downwards over a packed bed of an inert packing such as Beri saddles 45, and stripped by countercurrent flow with nitrogen introduced near the bottom of the WWS. The vapor overhead from WWS is incinerated. The bottoms from the WWS is pumped by pump P3 to further waste treatment, then disposed of in a suitable manner.

The freezing curve for aqueous caustic soda solutions has been provided by Landolt & Bornstein 4th Ed, 487–88 (1912); and the data for solubility of sodium chloride in caustic soda solutions as a function of temperature is provided by *Solubilities of Inorganic and*

*Metal-Organic Compounds* by W. F. Linke, American Chemical Society, Washington, D.C. (1965). The solubilites of Na in VCM, H₂O in VCM, and VCl in caustic/salt solutions at concentrations below 10% by wt of NaOH or NaCl as a function of temperature, are set forth in Table IV herebelow.

TABLE IV

| Temp °C./°F. | NaOH wt % | NaCl wt % | VCM/H$_2$O ppm | H$_2$O/VCM ppm | Na/VCM ppm |
|---|---|---|---|---|---|
| 10.3/50.5 | 9 | 4 | 398 | — | |
| 10.6/51.1 | 3 | 1 | 1848 | 336 | 0.04 |
| 10.3/50.5 | 5 | 2 | 1273 | 363 | 0.07 |
| 10.5/50.9 | 9 | 1 | 665 | 360 | 0.12 |
| 11.0/51.8 | 9 | 3 | 468 | 316 | 0.04 |
| 2.6/36.7 | 9 | 2 | 618 | 145 | 0.03 |
| 1.8/35.2 | 5 | 1 | 1483 | 120 | 0.04 |
| −6/21 | 9 | 1 | 725 | 81 | 0.05 |
| −4/25 | 7 | 1 | 1385 | 98 | 0.24 |
| −4/25 | 3 | 1 | 3165 | — | 0.16 |
| −4/25 | 7 | 3 | 1280 | — | 0.33 |
| −4/25 | 9 | 4 | 888 | — | 0.21 |

It will be seen from the above Table IV that there is less than 100 ppm water present in VCM when the temperature is below −4° C., and the conc of NaOH is greater than 3 wt %. Higher concentrations of NaOH are preferred to minimize the solubility of VCl in the aqueous caustic/salt solution, to provide a greater difference in specific gravities of the two phases for ease of phase separation, and to provide for situations where it might be necessary to neutralize greater concentrations of HCl in the VCl.

Figure 3:
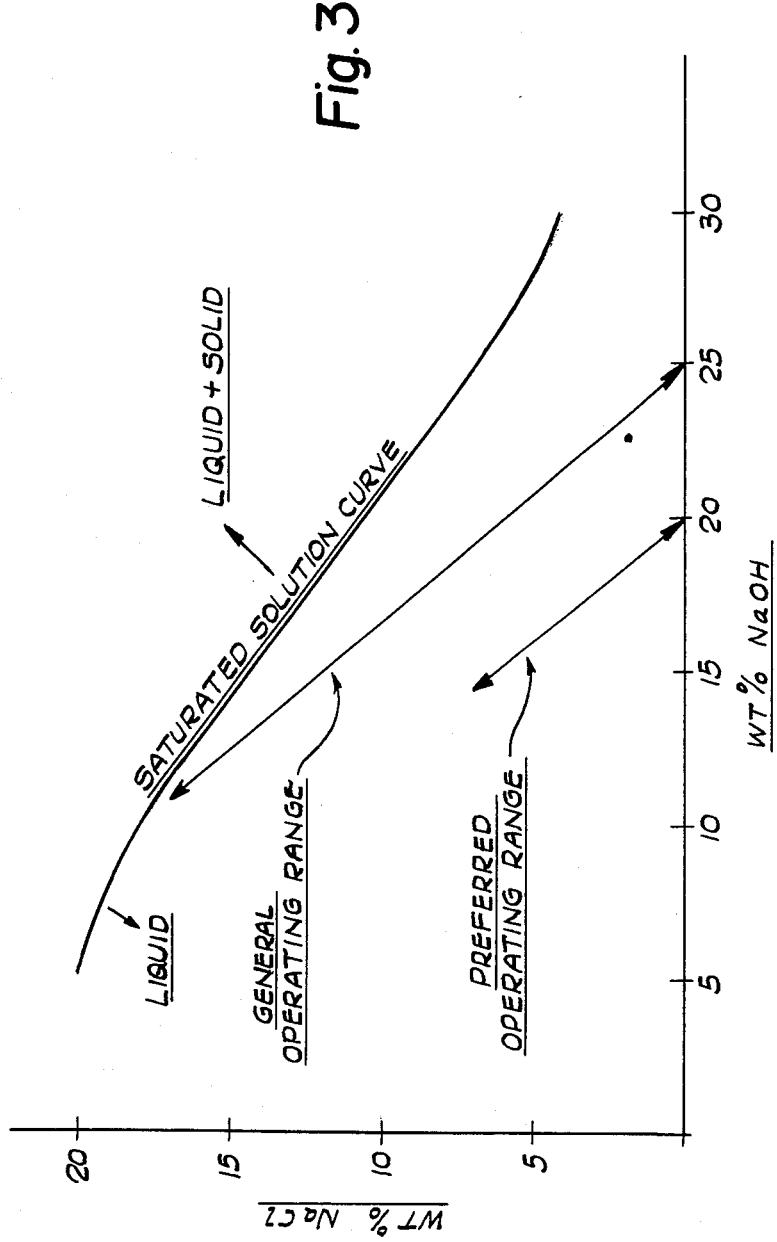
FIG. 3 is a graph in which the solubility of caustic soda (NaOH), and sodium chloride (NaCl) in water at a temperature in the range −21° C. to 0° C. are plotted.

Referring now to FIG. 3 there is shown a graph in which the solubility of NaOH—NaCl—H₂O system is plotted for the temperature range −6° F. to 32° F. It is found that only the relatively small portion, indicated by the dual-headed arrow labeled "Preferred Operating Range" of the caustic wash is particularly suitable for the process of this invention. It is seen that there is a wide range of concentrations of NaOH and NaCl in which the solutions remain liquid in the temperature range indicated (covered by the dual-headed arrow labeled "General Operating Range"), but only a smaller portion of that range proves to be particularly desirable. Each of the arrows was derived using data from the "Freezing Point Curve for Aqueous NaOH Solutions" supra on the assumption that the starting concentration of NaOH solution would be 20% and 25% respectively. It should be recognized that there will be further latitude for operation of the process at even lower temperatures than indicated because of the depression of freezing point due to the presence of NaCl which is not accounted for.

Experimental Procedure for Solubility Measurements

The solubilities of water and sodium salts in VCM, and of VCM in NaOH/NaCl solutions, were measured over a temperature range of 21°–51° F. for various concentrations of aqueous solutions containing from 3 to 9 wt % NaOH plus 1 to 4 wt % NaCl.

Measurements were made using an equilibrium cell which consisted of a one liter, double jacketed, glass reactor provided with a stirring means for vigorous stirring, and connected to to a low temperature thermosted bath with a circulating pump. The reactor contained all the necessary ports and valves for the introduction of liquids and withdrawal of samples from either the organic or liquid phases, and was also fitted with a standard mercury thermometer for measuring the temperature.

In a typical experimental run, 150 ml of a NaOH/NaCl aqueous solution were introduced into the reactor which had been previously evacuated, followed by 700 g of VCl liquid. The system was then allowed to equilibrate at the preselected temperature, while being vigorously stirred for 20 min. When stirring was stopped, the organic and aqueous phases separated, and samples for analyses were withdrawn from each phase.

About 400 g of the organic phase was taken from the top of the reactor, through a movable dip tube, into a preweighed, one liter, stainless steeel cylinder fitted with required valves and fittings. The sample was used for the determination of equilibrium concentrations of water and sodium in vinyl chloride.

For the determination of the equilibrium concentration of vinyl chloride in the NaOH/NaCl aqueous solutions, 8 ml samples were taken from the bottom of the reactor, through a tube fitted with a rubber septum, by means of a pressure lock syringe. The sample was transferred into preweighed, rubber capped bottles and care was taken to minimize the head space in the bottles.

Solubility of Water in Vinyl Chloride

Analysis of the equilibrium concentration of water in vinyl chloride was performed by gas chromatography with the method of standard addition.

After reweighing the cylinder containing the sample of vinyl chloride, a smaller (100 ml) cylinder provided with valves and a rubber septum was atached to the sample container. Exactly 1.0 ml of cyclohexane, used as an internal standard, was introduced through the septum, the valve separating the cylinders was opened, and the cyclohexane was thoroughly mixed with the vinyl chloride. Liquid samples of 6 microliter volume were drawn from the small cylinder with a high pressure microsyringe provided with a valve and then injected nto the gas chromatograph.

A Varian GC with thermal conductivity detector was used with 30 ml/min helium as the carrier gas and a six foot long, 0.125 inch Porapak Q, stainless steel column. Temperature programming included the initial temperature of 100° C. for .3 min, heating at the rate of 15° C./min, and final temperature of 180° C. Typical retention times for water, vinyl chloride, and cyclohexane were 1.05, 2.74 and 13.05 min, respectively.

The water content was determined by the method of standard addition, wherein known amounts of water were added sequentially to the cylinder in a manner similar to that described for the addition of the internal standard. The original water content was then determined graphically by linear extrapolation of the data through the axis.

Solubility of Sodium in Vinyl Chloride

Analysis of the equilibrium concentration of sodium in vinyl chloride was performed by atomic absorption spectrophotometry.

The total content of the sample cylinder was slowly poured as liquid into a flask containing 150 ml of distilled water and the vinyl chloride was allowed to vaporize and leave any sodium salts in the water phase. The water sample was then taken to a volume of 250 ml with distilled water after adding sufficient KCl as an ionization suppressor to obtain a concentration in potassium of 1000 ppm.

The water samples were subsequently analyzed for sodium concentration with a Perkin Elmer 403 AA spectrophotometer, and sodium standards were used to produce a calibration curve in the concentration range of the unknown samples.

Solubility of vinyl chloride in aqueous NaOH/NaCl Solutions

Analysis of the equilibrium concentration of VCM in the aqueous NaOH/NaCl phase was performed by gas chromatography after adding a known amount of ethanol as an internal standard.

A Perkin Elmer 3920 GC with flame ionization detector was used with a 12 foot long, 0.125 inch stainless steel column of 0.2% Carbowax 1500 on Carbopac C.

We claim:

1. In a process for purifying HCl- and water-containing vinyl chloride containing from 1 to 500 parts per million (ppm) HCl and 100 ppm to 300 ppm water dissolved therein, so as to produce essentially dry vinyl chloride monomer containing essentially no HCl, the improvement comprising, (a) contacting said vinyl chloride in the liquid phase with a strongly alkaline aqueous solution of an alkali metal hydroxide containing from about 5 to about 35% by wt of said alkali metal hydroxide, so as to form an intimate mixture of organic and aqueous phases at a temperature in the range below about 25° F. but above the freezing point of said solution, the amount of said solution being sufficient to neutralize said HCl and decrease the water in said vinyl chloride monomer to a concentration no greater than 100 ppm, and, (b) separating said organic phase from said aqueous phase, whereby said vinyl chloride monomer is dry and essentially free from HCl.

2. The process of claim 1 wherein said HCl- and water-containing vinyl chloride and said alkali metal hydroxide solution are continuously contacted, and continuously separated as organic phase and aqueous phase respectively by settling in a settling tank in which the residence time is in the range from about 5 min to about 20 min.

3. The process of claim 2 wherein said mixture of phases is at a temperature in the range from about 5°–25° F., and said alkali metal hydroxide solution contains from about 5 about 25 wt % of said alkali metal hydroxide.

4. The process of claim 3 wherein said wet, HCl-containing vinyl chloride to be purified is fed from a vinyl chloride column in the purification section of a vinyl chloride facility, and essentially dry product vinyl chloride monomer is heat exchanged with said vinyl chloride to be purified.

5. The process of claim 4 wherein said wet, HCl-containing vinyl chloride and said alkali metal hydroxide solution are mixed in static mixers so as to produce droplets of said organic phase in the size range from about 10 microns to about 1000 microns in diameter.

6. The proces of claim 5 wherein said alkali metal hydroxide solution is sodium hydroxide solution containing from about 10 to about 25% by wt of sodium hydroxide.

* * * * *

UNITED STATES PATENT AND TRADEMARK OFFICE
CERTIFICATE OF CORRECTION

PATENT NO. : 4,642,400

DATED : February 10, 1987

INVENTOR(S) : Joseph A. Cowfer and James E. Best

It is certified that error appears in the above—identified patent and that said Letters Patent is hereby corrected as shown below:

Column 6, line 58, "Beri saddles 45," should read -- Berl saddles 45,-- .

Column 6, line 64, "The freezing curve for aqueous caustic soda solutions", should read -- The freezing point curve for aqueous caustic soda solutions -- .

Signed and Sealed this

Twenty-sixth Day of July, 1988

Attest:

DONALD J. QUIGG

Attesting Officer

Commissioner of Patents and Trademarks